US00PP20233P3

(12) United States Plant Patent
White

(10) Patent No.: US PP20,233 P3
(45) Date of Patent: Aug. 25, 2009

(54) ROSE PLANT NAMED 'SAVASLEEP'

(50) Latin Name: *Rosa hybrida*
Varietal Denomination: SAVasleep

(75) Inventor: Wendy White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 246 days.

(21) Appl. No.: 11/416,610

(22) Filed: May 3, 2006

(65) Prior Publication Data

US 2007/0261141 P1 Nov. 8, 2007

(51) Int. Cl.
*A01H 5/00* (2006.01)

(52) U.S. Cl. ..... Plt./120
(58) Field of Classification Search ..... Plt./120
See application file for complete search history.

*Primary Examiner*—Annette H Para

(57) ABSTRACT

'SAVasleep' is a new and distinct variety of rose plant primarily identified by its fully double and very fragrant blooms of a dark to medium salmon-pink color. The flowers last very well on the plant and, as cut flowers. It has proven to be easy to care for with its above average disease resistance.

1 Drawing Sheet

CROSS REFERENCE

The cultivar from this same breeding program bearing some resemblance to this new invention is 'SAVapeach' (U.S. Plant patent application Ser. No. 10/306,392, abandoned). Both cultivars have fragrant and fully double flowers on plants that grow wider than tall. Their relationship is each one has the roses 'Little Darling' (U.S. Plant Pat. No. 1,581, expired) and 'KORtember' (Kordes, 1981, not under patent protection in the United States) in their background. 'Little Darling' is a floribunda with yellow and pink blended flowers on a very well branched plant with abundant bloom production throughout the growing season. Both 'SAVapeach' and this new invention are well branched and bloom abundantly throughout the growing season. The seed-parent of this new invention was a seedling of Party Girl (U.S. Plant Pat. No. 4,598, expired) by 'SAVaspark' (U.S. Plant Pat. No. 9,799). 'Party Girl' is a seedling of 'Rise 'n' Shine' (U.S. Plant Pat. No. 4,231, expired) by 'MORsheri' (U.S. Plant Pat. No. 3,826, expired). The seed parent of both 'Rise 'n' Shine' and 'MORsheri' is Little Darling. The seed parent of Peach Delight was 'MORsegold' (U.S. Plant Pat. No. 6,617, expired). The seed parent of 'MORsegold' is a seedling of 'Little Darling' by 'Lemon Delight' (U.S. Plant Pat. No. 4,447, expired). 'Kortember' is a strongly fragrant hybrid tea rose with orange-pink flowers. Both 'SAVapeach' and this new invention are fragrant. The pollen parent of this new invention was 'MACgenev' (U.S. Plant Pat. No. 8,279). The seed parent of 'MACgenev' is 'KORtember'. The pollen parent of 'SAVapeach' is 'Kortember'. Though the above similarities may be visually noted, there are also visual differences between 'SAVapeach' and this new invention. 'SAVapeach' has blooms of an apricot-blend and the new invention has salmon-pink flowers. 'SAVapeach' has stronger canes but a number of them grow outward at an angle up to 85° from perpendicular, this new invention has a more upright growing habit.

RIGHTS TO THE INVENTION

Be it known that I, Wendy R. White, of Ipswich, Mass., claim invention of new and useful improvements in ROSE PLANT/var. 'SAVasleep' and following is a clear and exact description of the same.

Genus and species: *Rosa hybrida.*

Varietal denomination: 'SAVasleep'.

BACKGROUND OF THE INVENTION

This present invention relates to a new and distinct variety of hardy, bush type rose plant. This new variety was developed by me under controlled conditions in a greenhouse in Rowley, Mass., by crossing the following two roses:

a seedling, which was previously developed by this same breeding program but never introduced, of 'Party Girl' (U.S. Plant Pat. No. 4,598) by 'SA Vaspark' (U.S. Plant Pat. No. 9,799) as seed parent;

the hybrid tea 'MACgenev' (U.S. Plant Pat. No. 8,279) as pollen parent

A single seedling was selected from this cross and given the code name of 'SAVaseep' with the trade name of Sleeping Beauty. It is classified as a Mini-Flora.

The idyllic goal of this breeding program was to produce unique miniature roses with the qualities of disease resistance, hardiness, fragrance and abundant bloom from late spring to late fall. Roses selected as pollen and seed parents for this program are chosen for having at least two of these qualities. These roses are crossed with miniatures having, primarily, abundant bloom production and, preferably, any or all of the other desired qualities. The seed parent chosen for this cross had abundant bloom production on a compact, miniature plant. The plant chosen as pollen parent, 'MACgenev', is known to be very fragrant, to have good disease resistance and to be winter hardy to zone 5. This new invention has been found to have good disease resistance, is hardy to at least zone 5, is fragrant and blooms almost continuously throughout the growing season. It was rather large for the miniature class into which it was first registered. It has since been reregistered into the Mini-Flora class that was created after 'SAVasleep' was introduced for sale.

Differences from the parents are visually obvious as the following chart depicts.

| | THIS PRESENT INVENTION, 'SAVASLEEP' | THE SEED PARENT OF 'PARTY GIRL' BY 'SAVASPARK' | THE POLLEN PARENT, 'MACGENEV' |
|---|---|---|---|
| CLASS | Mini-Flora | Miniature | Hybrid tea |
| BLOOM COLOR | Full open bloom: Medium to dark pink-a bit darker than either parent | Full open bloom: Medium to dark pink | Full open bloom: Medium to dark pink |
| BLOOM HABIT | Borne singly and in small clusters; larger clusters on candelabra stems; near continuously, throughout the season; | Borne in large sprays and clusters; near continuously, throughout the season; | Borne primarily singly; repeats in cycles |
| PETALAGE | 45 to 55 | 10 | 25 to 30 |
| FRAGRANCE | Strong | Not significant | Very Fragrant |
| PLANT HABIT | Upright and spreading, width becoming about twice its height | Upright | Upright |

Asexual reproduction by cuttings of this new invention in both Rowley, Mass. and Arroyo Grand, Calif., shows that all distinguishing characteristics of this rose continually come true to form.

SUMMARY OF THE INVENTION

This present invention relates to a new and distinct variety of hardy, low growing, bush type rose plant. The characteristics distinguishing it from its parents and from all other cultivars, of which I am aware, are its unique combination of flower form, flower size, petal count, fragrance and color combined with its plant habit, size and color of foliage, and its degree of disease resistance. Specific distinguishing characteristics are:

Classic hybrid tea form flower and bud.

Fully double, dark to medium salmon-pink flowers that last well on the plant and as cut flowers.

Moderate to strong, sweet fragrance.

Medium green, semi-glossy foliage.

A bushy and upright plant that can grow to a three-foot spread but generally only fifteen to eighteen inches tall. Some locations may see it send up individual canes that reach up to three feet tall.

Above average disease resistance.

BRIEF DESCRIPTION OF THE DRAWING

The accompanying color photograph, taken with artificial lighting in February, shows specific parts of this new invention as described under BOTANICAL DESCRIPTION OF THE PLANT, including specimens of the flowers of this new variety in different stages of development, from bud to full open bloom, with sepals, young and older foliage and stems with some prickles, taken from 6 to 7 year old plants as grown under shaded plastic in a greenhouse in Arroyo Grande, Calif. Lying on the table in front of the flowers is a candelabra-type stem. At the back of the arrangement are laterals or flowering stems from a candelabra-type stem, each with a single bud. The inset picture at the lower right corner of the photograph was taken in natural daylight and is of flowers grown in a plastic covered greenhouse with a roof that is opened during the day, weather permitting.

BOTANICAL DESCRIPTION OF THE PLANT

The following observations, measurements, values and comparisons describe 3 and 6 year old plants of 'SAVasleep', grown in 2 and 3 gallon nursery containers in plastic covered and shaded greenhouses in Arroyo Grande, Calif. The information about the rose hips and some about the reproductive organs of this cultivar were taken from plants grown in a plastic covered greenhouse in Rowley, Mass. Color references are using The Royal Horticultural Society Colour Chart, except where common terms of color are used.

FLOWERS

BLOOMING HABIT is long bloom cycles with a fast repeat. Flowers are borne mostly singly but also in clusters of two or three. Clusters on candelabra growth, when present, are pyramidal with 5 to 9 blooms or more in each cluster. (Candelabras are discussed in length near the end of the section describing the plant in the paragraph entitled "VARIATIONS".)

BUD form is cuneate with an attenuate apex. The length of the bud averages ½ inch and the diameter varies from ⅜ inch to 7/16 inch, just before the sepals divide.

SEPALS: Flowers have five or six sepals. The outer surfaces are matte and a medium green color, between 144A and 138B. Inside surfaces have a pubescent covering and are a color between 191B and 191C, from the Greyed-Green Group, with a basal area of light yellow-green, nearest 145C.

The sepals extend beyond the tip of the bud by ½ to ⅝ inch. The outer sepals are 1⅛ to 1¼ inches long and 9/32 inch wide at the widest point. A typical outer sepal with a length of 1⅛ inches has a cuneate form upward from the base for ½ inch, becomes attenuate for 5/16 inch and has a 5/16 inch spindle-like apex. Two innermost sepals vary in length from ⅞ inch to 1 3/16 inch having attenuate apices and are ¼ to 5/16 inch wide at the widest point. The one or two sepals in-between the inner and outer sepals usually vary from 1 3/32 to 1 3/16 inches long and are 9/32 or 10/32 inch wide. The edges of the margins are ciliated.

Sepals roll back ahead of the petals to perpendicular to the receptacle and the tips slightly recurve. They drop from the plant with the petals.

The RECEPTACLE is funnel to urn shaped with a diameter of 5/16 to ⅜ inch and a height of ⅜ inch. The surface is medium green, between 138B and 143C, and semi-glossy, with long soft, upright hairs. The top surface is circular with an 11/32 inch diameter and an alveola in the center measuring 7/32 inch diameter. The color of the top surface is near 160C from the Greyed-Yellow Group.

PEDUNCLES are straight and strong, varying in length from 1⅝ inches to 2 inches and having a diameter most often of 7/64 inch. Their color is a Scheele's Green, nearest 143C. Attached to the base of the peduncle is often a narrow, single leaflet at the end of a petiole with a pair of stipules attached the entire length of the petiole. The tips of these stipules angle out at 15 to 40 degrees from the petiole.

BLOOM: Diameter of a full open bloom is three inches with a 1¾ inches height. At exhibition stage the diameter is between 1⅞ and 2⅛ inches. When full-blown and petals are starting to fade the diameter is 3½ inches with a profile height of 1½ to 1⅝ inches.

PETALS: There are 45 to 55 petals of a medium thickness with a velvety upper surface and satiny lower surface. The shape of the outer petals is broad fan-shaped with an arcuate outer margin and an acute tip at the apex having a notch on either side of it. The size of the outer petals in a full-blown flower varies from 1⅜ to 1¾ inches wide and 1¼ to 1 1/16 inches long.

The color first visible as the sepals begin to open is a deep color between 43B and near 51A, both from the Red Group. As the petals unfurl, the color lightens slightly to between 43B and 52B. The first few days the petals become between 43C and 52C on the upper surface with the under surface nearest 43D, which is a Scarlet. The basal area on the upper surface is near 14C, Lemon Yellow. The reverse of the petals may have a near white streak up the middle.

Half open the upper surface becomes nearest 43D and a little lighter on the under surface, between 49B and 38B. The yellow of the basal area has lightened to Chrome Yellow, near 14D, and is only visible as the first outer petals open. As succeeding petals unfurl the basal area becomes concealed from view.

Full open blooms show a near uniform color between 52C and 43D. The basal area of the petals is Chrome Yellow on the inner petals and much lighter on the outer petals becoming near 158B. The reverse of the petals has lightened to a color between 39D and 55C.

PETALOIDS have the same coloring and texture as the inner petals, and additionally many have near white, nearest 158D, streaking up through the middle on both surfaces. The outer margins will often look tattered or torn especially when there is a white streak up through the center of the petaloid.

GENERAL TONALITY of this rose is a dark salmon-pink. After several days the bush would appear to have both dark to medium salmon-pink and medium to light salmon-pink blooms. From a distance there appears to be both dark and medium salmon-pink blooms on the plant.

QUALITY OF BLOOM: Petals are of a medium thickness. The bloom on the plant usually remains fresh for well over a week, depending on climatic conditions. The petals drop cleanly from the plant. As cut flowers they can last 10 days and more.

REPRODUCTIVE ORGANS

STAMENS are regularly attached along the outer edge of the receptacle, adjacent to the petals. The quantity varies from 120 to 148. The filaments are 8/32 to 9/32 inch long and a medium yellow color of near 3C. Anthers are near a light yellow-orange with pollen sacs of a medium yellow-orange.

There are around 40 to 60 PISTILS located in the alveola in the top of the receptacle. The styles are thin and straight, varying from 3/16 to 5/16 inch long. The color is nearest 158D from the Yellow-White Group. The stigmas are nearest 158C.

The HIPS are pear shaped with a diameter of around 9/16 inch at the widest part. The color when mature is near 30C, Saturn Red, with one or more seeds protruding from the top of near 160D. There averages around 8 medium-sized seeds per hip.

PLANT

The plant of 'SAVasleep' is generally upright; the general height is fifteen to eighteen inches while the width can become two to three feet. Branching originates from a main cane. Growth is vigorous. The length of the internodes on the main cane is 1½ inches; on the primary laterals it is about 1 inch, usually with four per stem; and on the flowering stem there are four to eight nodes around 1⅛ inches apart plus two or three additional nodes at the base of these stems that are closer together than that by varying amounts.

FOLIAGE is pinnately compound with five leaflets and occasionally three. The shape of the leaflets is narrow-ovate. The terminal leaflet will sometimes have a narrow base giving it the overall shape of oblong with an acute tip. The size of the leaflets and the length of the rachis are usually largest towards the top of the plant, with the shortest leaflets on the leaves located near the base of each stem. The length of the mature leaf ranges from 3 11/16 to 4 inches. The size of the mature terminal leaflet generally ranges from 1¼ to 1⅝ inches long and ¾ to 13/16 inch wide. The upper surface is semi-glossy and glabrous. The main veins are completely recessed. The primary lateral veins are completely recessed at the juncture with the main vein, which decreases toward the margin where they are only slightly recessed. The underside of the leaflets is matte and leathery. Here, the main vein protrudes completely. The primary lateral veins protrude entirely where they connect to the main vein and decreasing to not protruding at all just before they reach the leaf margin, and the secondary laterals protrude only slightly. Margins have a fine, double and uneven serration. Each serrate is tipped with a gland.

There is anthocyanin coloring present on the young foliage. The upper surface is a medium green, nearest 138A, with flushing of grayed-purple, near 187B, concentrated near the margins. The under surface is nearest 138B, usually flushed lightly with near 187C. The main vein and margins are flushed darker, near 187B. The color of the older foliage is dark green, near 139A, and the under surface is near 191A from the Greyed-Green Group with the main veins between 149D and 139D PETIOLES vary in length from inch 1 1/16 to 1 5/16 inches with a diameter most often of 3/32 inch. There is anthocyanin coloring on the young growth. The color on the older leaves is near 139A along the ridges and nearest 148D, a medium color from the Yellow-Green Group, in the groove. The undersides may be nearest 138A or 138B.

RACHIS: The length of the rachis is most often ⅝ inch but has been measured up to ⅞ inch. The color on the upper side of mature leaves is dark green along the ridges, near 139A, and light green, near 145B, in the groove. The underside is a light yellow-green, between 139D and 149D. There is most often a prickle at or near the point where the leaflets are attached.

PETIOLULES are nearest a dark green, 137B, along the ridges and 145B in the groove with the exception that the groove of the petiolule to the terminal leaflet is near 145B but becomes near 145C just before entering into the terminal leaflet. The underside is between 139D and 149D. The length to the terminal leaflet is around ⅞ inch and to the other leaflets is 1/16 inch.

STIPULES are attached one to each side of the petiole in near even pairs. The length is most often ½ inch attached and 3/16 inch angled outward at 45 degrees adaxial, with the tips recurving inward toward each other. Margins are lined with stipitate glands giving them a pectinate appearance. The edges usually recurve tightly, although they occasionally lay flat. The color is near 148C, a light olive-green, where they are attached to the petiole, a darker green, between 138A and 139B along the outer edges, and the tips are very dark green, nearest 139A. The reverse is nearest 138B.

WOOD: The diameter of the main stems is 7/32 inch and that of the laterals is around 1/8 inch. The color of the new wood is near 138A and the old wood is between 137A and 139A. The surfaces of both old and new stems are glabrous.

PRICKLES: On the main stalks there are two or three prickles between nodes, usually within 1/2 inch of the upper node. Their length varies between 1/4 inch and 9/32 inch. On laterals there may be one prickle between nodes but most often there are none. On flowering stems there may be one between the nodes nearest the base of the stem and within 1/4 inch of the higher of two nodes, otherwise there are none. Their length varies from 5/32 inch to 1/4 inch. Prickles have a very slight arch downward as they taper to a point, and an oval base measuring about 3/16 inch long on the main cane. Their color when young is nearest 182C from the Greyed-Red Group and near translucent. When old the color becomes between 177A and 177B, a medium brown from the Greyed-Orange Group. On the rachis/petiole the color is a medium green, near 138C.

VARIATIONS: A difference in day and night temperatures greater than around 30 degrees will cause the plant to send up long, fast growing canes. These usually originate at or near the base of the plant and are often referred to as candelabras because of the large number of blooms originating near the top of a usually long and straight cane. On this new invention these canes have been observed up to 36 inches long and always terminate in a large, loose spray. Often the flowering stems within that spray terminate in a small cluster of two or more flowers. The length of the internodes on these canes has most often been measured at 1 7/8 inches. The length of mature leaves on these canes was measured around 4 3/4 inches. Terminal leaflets have been measured around 1 1/16 inches at the widest point, 2 3/16 inches in length and with a petiole length varying between 1 inch and 1 5/16 inches. Stipules average 21/32 inch attached and 8/16 to 9/16 inch angled outward. The diameter most often found on these candelabra-type stems is 17/64 inch on the main canes. Laterals may originate on the upper third of these canes and usually have a diameter of 3/16 inch. Prickles on the main canes range from four between nodes near the base, then to three between nodes, and closer to the top of these canes there are only one or two between nodes. On the main canes they are about 7/16 inch long and on the laterals they measure 1/4 inch long. Their form is attenuate with a slight angle down. The color when young is between 166A and 175A, an orange-brown. When old the color becomes a bit lighter and with less orange, near 177A.

RESISTANCE: This new cultivar has proven to be highly resistant to blackspot, and powdery and downy mildews. Rust has not been observed and it would appear to have at least some resistance to rust. Aphids and spider mites have not proven to be a problem for this cultivar, indicating some resistance.

WINTER HARDINESS: 'SAVasleep' has been tested winter hardy to zone 5 with winter protection. Heat Tolerance has been tested through heat zone 8.

What is claimed is:

1. A new and distinct variety of hardy rose plant is claimed, substantially as illustrated and described, with long lasting and sweetly fragrant, salmon-pink flowers borne on a vigorous plant and having over-all good disease resistance and suitable for production from softwood cuttings.

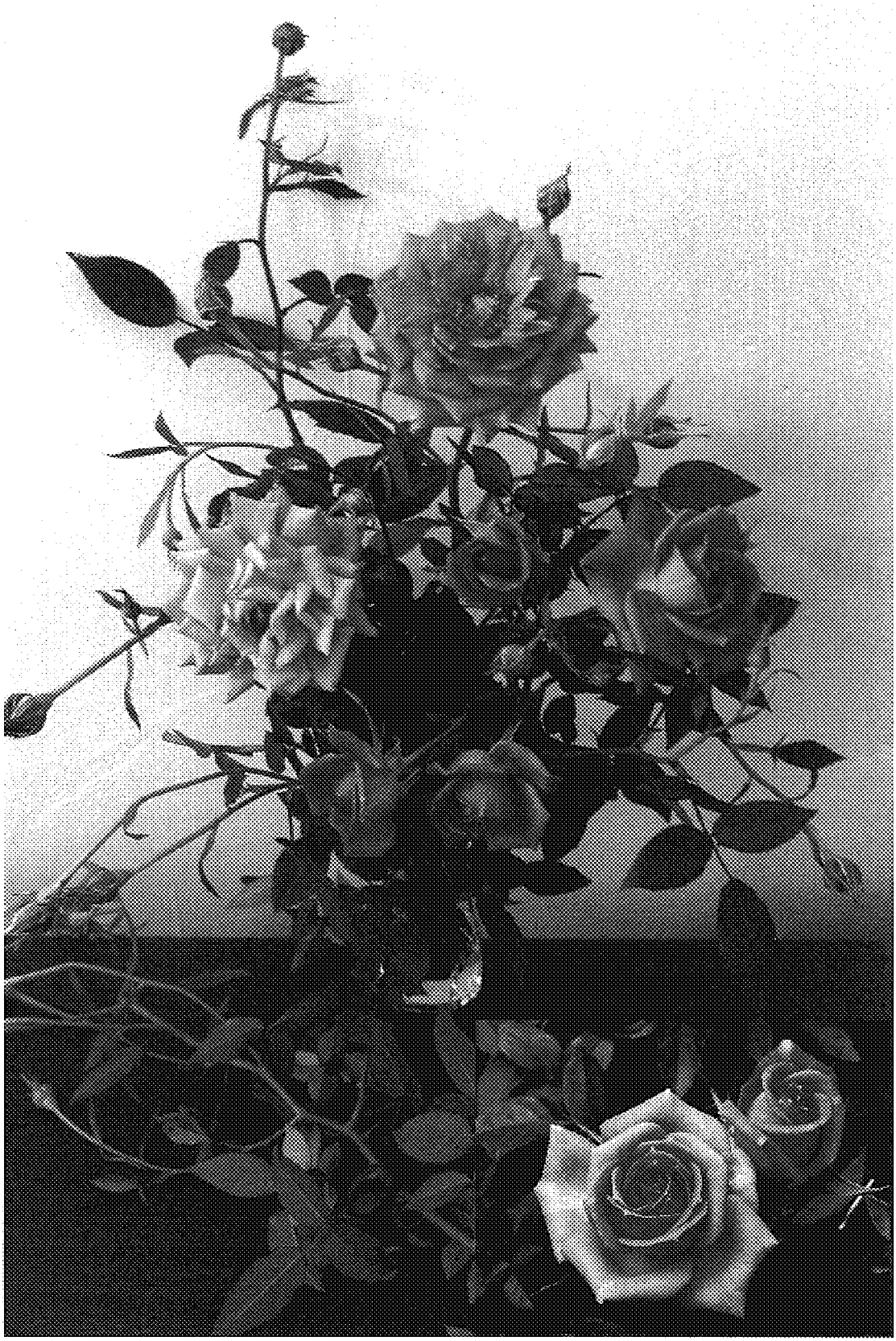

* * * * *